(12) United States Patent
Kim

(10) Patent No.: US 10,729,473 B2
(45) Date of Patent: Aug. 4, 2020

(54) SYSTEM FOR FIXING CERVICAL VERTEBRAE AND A DRIVER USED FOR AN APPARATUS FOR FIXING CERVICAL VERTEBRAE

(71) Applicant: KYUNGPOOK NATIONAL UNIVERSITY INDUSTRY-ACADEMIC COOPERATION FOUNDATION, Daegu (KR)

(72) Inventor: Kyoung Tae Kim, Daegu (KR)

(73) Assignee: KYUNGPOOK NATIONAL UNIVERSITY INDUSTRY-ACADEMIC COOPERATION FOUNDATION, Daegu (KR)

(*) Notice: Subject to any disclaimer, the term of this patent is extended or adjusted under 35 U.S.C. 154(b) by 262 days.

(21) Appl. No.: 14/938,286

(22) Filed: Nov. 11, 2015

(65) Prior Publication Data
US 2016/0128738 A1    May 12, 2016

(30) Foreign Application Priority Data
Nov. 11, 2014    (KR) .................. 10-2014-0156191

(51) Int. Cl.
*A61B 17/70*    (2006.01)
*A61B 17/88*    (2006.01)
(Continued)

(52) U.S. Cl.
CPC ...... *A61B 17/7059* (2013.01); *A61B 17/7082* (2013.01); *A61B 17/8038* (2013.01);
(Continued)

(58) Field of Classification Search
CPC ............ A61B 17/7059; A61B 17/8042; A61B 17/8033; A61B 17/8047; A61B 17/8038;
(Continued)

(56) References Cited

U.S. PATENT DOCUMENTS

| 4,027,932 A | 6/1977 | Kunkel et al. |
| 4,359,318 A | 11/1982 | Gittleman |

(Continued)

FOREIGN PATENT DOCUMENTS

| JP | 2011-139901 A | 7/2011 |
| JP | 2014-517739 A | 7/2014 |

(Continued)

*Primary Examiner* — David W Bates
*Assistant Examiner* — Marcela I Shirsat
(74) *Attorney, Agent, or Firm* — Novick, Kim & Lee, PLLC; Sang Ho Lee

(57) ABSTRACT

A fixing system for cervical vertebrae includes a fixing apparatus for cervical vertebrae in which a cervical vertebrae-fixing plate is made close contact with cervical vertebrae and a screw is inserted into the cervical vertebrae through a screw hole formed in the cervical vertebrae-fixing plate, and a driver that rotates the screw. Here, clips for holding the inserted screw are provided in the screw hole, a convex portion is positioned at the rear of a front end portion of the driver which is fitted in a groove on the screw, and the driver loosens the inserted screw while spreading the clips using the convex portion, when the inserted screw is loosened.

5 Claims, 2 Drawing Sheets

(51) Int. Cl.
  *A61B 17/80* (2006.01)
  *A61B 17/86* (2006.01)
(52) U.S. Cl.
  CPC ...... *A61B 17/8047* (2013.01); *A61B 17/8615* (2013.01); *A61B 17/888* (2013.01); *A61B 17/8886* (2013.01); *A61B 17/8875* (2013.01); *A61B 17/8894* (2013.01)
(58) Field of Classification Search
  CPC ............ A61B 17/7082; A61B 17/8875; A61B 17/8886; A61B 17/8894
  USPC ............ 606/289–290; 29/229, 268, 228, 225
  See application file for complete search history.

(56) References Cited

U.S. PATENT DOCUMENTS

| | | | |
|---|---|---|---|
| 4,474,516 A | 10/1984 | Schiefer | |
| 4,678,383 A | 7/1987 | Bergner | |
| 5,127,407 A | 7/1992 | Tan | |
| 5,265,504 A * | 11/1993 | Fruhm | B25G 1/085 81/177.4 |
| 6,171,311 B1 | 1/2001 | Richelsoph | |
| 6,249,946 B1 * | 6/2001 | Greenhill | B25B 27/20 29/229 |
| 6,258,089 B1 * | 7/2001 | Campbell | A61B 17/7059 606/287 |
| 6,290,701 B1 | 9/2001 | Enayati | |
| 6,331,179 B1 * | 12/2001 | Freid | A61B 17/7059 606/279 |
| 6,402,757 B1 | 6/2002 | Moore, III et al. | |
| 6,436,100 B1 | 8/2002 | Berger | |
| 6,652,525 B1 | 11/2003 | Assaker et al. | |
| 6,767,350 B1 | 7/2004 | Lob | |
| 6,778,861 B1 | 8/2004 | Liebrecht et al. | |
| 7,029,472 B1 | 4/2006 | Fortin | |
| 7,194,314 B1 | 3/2007 | Richter et al. | |
| 7,235,100 B2 | 6/2007 | Martinek | |
| 7,302,298 B2 | 11/2007 | Lowry et al. | |
| 7,662,154 B2 | 2/2010 | Ribeiro | |
| 8,057,521 B2 | 11/2011 | Smisson, III et al. | |
| 8,419,777 B2 | 4/2013 | Walker et al. | |
| 8,454,667 B2 | 6/2013 | Humphreys | |
| 8,628,325 B2 | 1/2014 | Vachtenberg | |
| 8,758,347 B2 | 6/2014 | Weiner et al. | |
| 8,906,077 B2 | 12/2014 | Bush, Jr. et al. | |
| 8,932,335 B2 | 1/2015 | Humphreys | |
| 8,940,030 B1 | 1/2015 | Stein et al. | |
| 8,956,394 B1 | 2/2015 | McDonnell | |
| 9,265,531 B2 | 2/2016 | Ziolo | |
| 9,629,664 B2 | 4/2017 | Altarac et al. | |
| 9,775,652 B2 | 10/2017 | Altarac et al. | |
| 9,918,749 B2 | 3/2018 | Altarac et al. | |
| 9,918,760 B2 | 3/2018 | Bush, Jr. et al. | |
| 9,943,341 B2 * | 4/2018 | Carnes | A61B 17/7059 |
| 2002/0040241 A1 | 4/2002 | Jarvinen | |
| 2002/0151899 A1 * | 10/2002 | Bailey | A61B 17/7059 606/86 B |
| 2003/0135274 A1 | 7/2003 | Hays | |
| 2003/0187440 A1 | 10/2003 | Richelsoph et al. | |
| 2004/0220571 A1 | 11/2004 | Assaker et al. | |
| 2004/0243207 A1 | 12/2004 | Olson et al. | |
| 2004/0267361 A1 | 12/2004 | Donnelly et al. | |
| 2005/0059972 A1 | 3/2005 | Biscup | |
| 2005/0192577 A1 | 9/2005 | Mosca et al. | |
| 2005/0216027 A1 * | 9/2005 | Suh | A61B 17/8888 606/104 |
| 2005/0261689 A1 | 11/2005 | Lin | |
| 2006/0106390 A1 | 5/2006 | Jensen et al. | |
| 2006/0149258 A1 | 7/2006 | Sousa | |
| 2006/0161157 A1 * | 7/2006 | Mosca | A61B 17/1615 606/294 |
| 2006/0217721 A1 | 9/2006 | Suh | |
| 2006/0235410 A1 | 10/2006 | Ralph et al. | |
| 2006/0247639 A1 | 11/2006 | Anderson | |
| 2006/0293670 A1 | 12/2006 | Smisson et al. | |
| 2007/0233071 A1 | 10/2007 | Dewey et al. | |
| 2008/0039846 A1 | 2/2008 | Lee et al. | |
| 2008/0161864 A1 | 7/2008 | Beck et al. | |
| 2008/0188897 A1 | 8/2008 | Krebs et al. | |
| 2008/0221624 A1 | 9/2008 | Gooch | |
| 2009/0125072 A1 | 5/2009 | Neubardt | |
| 2009/0318970 A1 | 12/2009 | Butler et al. | |
| 2010/0036467 A1 | 2/2010 | Kraus et al. | |
| 2010/0049256 A1 | 2/2010 | Jeon et al. | |
| 2010/0106198 A1 | 4/2010 | Adcox et al. | |
| 2010/0121383 A1 | 5/2010 | Stanaford et al. | |
| 2011/0022097 A1 | 1/2011 | Walker et al. | |
| 2011/0029023 A1 | 2/2011 | Tornier | |
| 2011/0106159 A1 | 5/2011 | Nazeck | |
| 2011/0144702 A1 | 6/2011 | Leroux et al. | |
| 2011/0152934 A1 | 6/2011 | Asaad et al. | |
| 2011/0230885 A1 | 9/2011 | Weiner et al. | |
| 2011/0264151 A1 | 10/2011 | Davis et al. | |
| 2012/0185001 A1 | 7/2012 | Nayet et al. | |
| 2012/0232595 A1 | 9/2012 | Holschlag | |
| 2012/0265258 A1 | 10/2012 | Garvey | |
| 2012/0271363 A1 | 10/2012 | Luxon et al. | |
| 2012/0289978 A1 | 11/2012 | Jacob | |
| 2013/0023936 A1 | 1/2013 | Altarac et al. | |
| 2013/0041413 A1 | 2/2013 | Sun | |
| 2013/0231704 A1 | 9/2013 | Larroque-Lahitette | |
| 2013/0304067 A1 | 11/2013 | Hess et al. | |
| 2013/0325074 A1 | 12/2013 | Ziolo | |
| 2014/0066997 A1 | 3/2014 | Humphreys | |
| 2015/0134013 A1 | 5/2015 | Paul | |
| 2015/0201982 A1 | 7/2015 | Altarac et al. | |
| 2015/0216573 A1 | 8/2015 | Chin et al. | |
| 2015/0230838 A1 | 8/2015 | Lazoglu et al. | |
| 2016/0166295 A1 | 6/2016 | Ziolo | |
| 2016/0206351 A1 | 7/2016 | Eom | |
| 2016/0278834 A1 | 9/2016 | Bayer | |

FOREIGN PATENT DOCUMENTS

| | | |
|---|---|---|
| KR | 1999-0035953 A | 5/1999 |
| KR | 10-2002-0082009 A | 10/2002 |
| KR | 1020040001287 A | 1/2004 |
| KR | 20-0367241 Y1 | 11/2004 |
| KR | 10-2005-0023111 A | 3/2005 |
| KR | 10-2007-0026472 A | 3/2007 |
| KR | 10-2007-0112200 A | 11/2007 |
| KR | 10-2008-0059920 A | 7/2008 |
| KR | 10-0850322 B1 | 8/2008 |
| KR | 10-2008-0105506 A | 12/2008 |
| KR | 10-0872529 B1 | 12/2008 |
| KR | 10-2009-0015933 A | 2/2009 |
| KR | 10-2009-0111774 A | 10/2009 |
| KR | 10-2010-0124709 A | 11/2010 |
| KR | 10-2012-0039622 A | 4/2012 |
| KR | 10-2012-0040309 A | 4/2012 |
| KR | 10-2012-0052265 A | 5/2012 |
| KR | 10-1142895 B1 | 5/2012 |
| KR | 10-2012-0057758 A | 6/2012 |
| KR | 10-2013-0004669 A | 1/2013 |
| KR | 10-2013-0015081 A | 2/2013 |
| KR | 10-2013-0016303 A | 2/2013 |
| KR | 10-1331429 B1 | 11/2013 |
| KR | 10-2014-0003938 A | 1/2014 |
| KR | 10-2014-0018796 A | 2/2014 |
| KR | 10-2014-0052320 A | 5/2014 |
| KR | 10-1413732 B1 | 7/2014 |
| KR | 10-2015-0120105 A | 10/2015 |
| WO | 2008/146981 A1 | 12/2008 |
| WO | 2009/105106 A2 | 8/2009 |

* cited by examiner

SYSTEM FOR FIXING CERVICAL VERTEBRAE AND A DRIVER USED FOR AN APPARATUS FOR FIXING CERVICAL VERTEBRAE

INCORPORATION BY REFERENCE

The instant application claims benefit of priority from Korean Patent Application No. 10-2014-0156191 filed on Nov. 11, 2014, the entire content of which is hereby incorporated by reference.

BACKGROUND

1. Field of the Invention

The present invention relates to a fixing system for cervical vertebrae and a driver used for a fixing apparatus for cervical vertebrae, and more particularly, to a driver which includes a convex portion for spreading clips provided in a screw hole of a cervical vertebrae-fixing plate and a fixing system for cervical vertebrae having the driver.

2. Discussion of Related Art

In general, cervical vertebrae are those positioned at the top of the spine with seven backbones and between the skull and the spine, and most cervical vertebrae are small and flat, and a foramen through which the vertebral artery (except seventh cervical vertebra), the veins, and the cervical sympathetic trunk pass is present in each transverse protrusion.

In addition, motor nerves which carry command information from the brain to the body parts such as legs and arms and sensory nerves which carry sensory information from the legs and arms and each body organ to the brain constitute the spinal cord and pass through the spinal canal present in the cervical vertebrae, and autonomic nerves which control heartbeat, breathing, and digestive functions pass in front of the cervical vertebrae and arteries which supply blood to the cerebrum pass on both sides of the cervical vertebrae.

The cervical vertebrae having the above-described structure and functions may cause damage thereto or deformation in a curved state thereof due to external impact caused by accidents or twisted posture that continues for a long time, and in this instance, a gap between neck bones constituting the cervical vertebrae is narrowed to press the nerves so that slight pain may be initially felt, and in the mid and late, it is attended by symptoms in which the body is paralyzed in addition to severe pain. As a result, illness such as cervical disc disease, cervical hernial disc, cervical spondylosis myelopathy, cervical fracture and dislocation, tumor, kyphotic deformity, and the like may be generated.

In the most common method for an operation for cervical vertebrae, a vertebral body of the disc in which a lesion is caused is removed, an artificial implant is inserted between the cervical vertebrae, and then a cervical vertebrae-fixing plate is put to the front side of the inserted artificial implant, and in this instance, a screw is inserted into the cervical vertebrae through screw holes formed in the cervical vertebrae-fixing plate and a fixing system for cervical vertebrae is used to prevent the inserted screw from being shaken or escaped backward (see Korean Patent Application No. 10-2011-0065853).

However, it often needs to remove the inserted screw in a process of the operation for cervical vertebrae such as in a case in which the inserted screw should be withdrawn because the size of the screw is not tailored, but the conventional apparatus for fixing cervical vertebrae only considers reliable and secure insertion of the screw without considering easier removal of the screw, and thereby it requires a lot of effort and time to remove the screw in the process of the operation for cervical vertebrae so that the operation time becomes longer and a smooth operation is not achieved.

In order to address these problems, the need for easier removal of the screw inserted into the cervical vertebrae has emerged.

SUMMARY OF THE INVENTION

The present invention is directed to a fixing system for cervical vertebrae in which an operation for cervical vertebrae may be smoothly performed by easily removing a screw inserted into cervical vertebrae, and a driver used for a fixing apparatus for cervical vertebrae.

Additional aspects of the invention will be set forth in part in the description which follows and, in part, will be obvious from the description, or may be learned by practice of the invention.

According to an aspect of the present invention, there is provided a fixing system for cervical vertebrae including: a fixing apparatus for cervical vertebrae in which a cervical vertebrae-fixing plate is made close contact with cervical vertebrae and a screw is inserted into the cervical vertebrae through a screw hole formed in the cervical vertebrae-fixing plate; and a driver that rotates the screw, wherein clips for holding the inserted screw are provided in the screw hole, a convex portion is positioned at the rear of a front end portion of the driver which is fitted in a groove on the screw, and the driver loosens the inserted screw while spreading the clips using the convex portion, when the inserted screw is loosened.

According to another aspect of the present invention, there is provided a loosening driver which is used for a fixing apparatus for cervical vertebrae in which a cervical vertebrae-fixing plate is made close contact with cervical vertebrae and a screw is inserted into the cervical vertebrae through a screw hole formed in the cervical vertebrae-fixing plate, and loosens the inserted screw, wherein clips for holding the inserted screw are provided in the screw hole, a convex portion is positioned at the rear of a front end portion of the loosening driver which is fitted in a groove on the screw, and the loosening driver loosens the inserted screw while spreading the clips using the convex portion, when the inserted screw is loosened.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
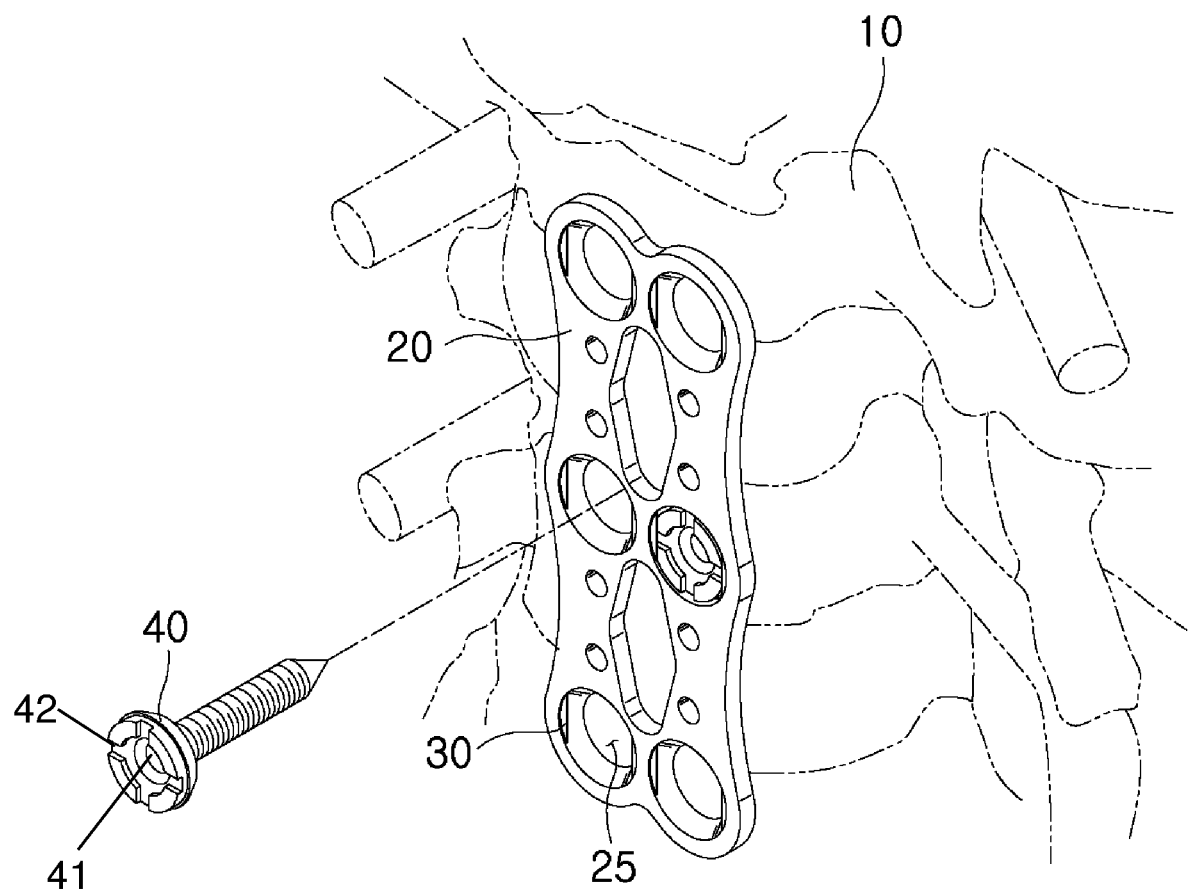
FIG. 1 shows a state in which a fixing apparatus for cervical vertebrae according to an embodiment of the present invention is mounted in the cervical vertebrae.

Hereinafter, preferred embodiments according to the present invention will be described with reference to the accompanying drawings.

However, the embodiments of the present invention can be modified in many different forms and the scope of the present invention is not limited to the embodiments described below. In addition, the embodiments of the present invention are provided to more completely explain the present invention to those skilled in the art. The present invention will only be defined by the scope of claims. The same reference numerals throughout the specification refer to like elements.

Terms used in the present specification are intended to illustrate the embodiments, and are not intended to limit the invention. In addition, as used herein, the singular forms "a," "an," and "the" are intended to include the plural forms, including "at least one," unless the content clearly indicates otherwise. In the specifications, it should be understood that the terms "comprising," or "including" when used in these specifications, specify the presence of stated elements, steps, and operations, but do not preclude the presence or addition of one or more other elements, steps, and operations thereof.

Figure 2:
FIG. 2 is a schematic view showing an insertion driver that is used for a fixing apparatus for cervical vertebrae according to an embodiment of the present invention.
Figure 3:
FIG. 3 is a schematic view showing a loosening driver that is used for a fixing apparatus for cervical vertebrae according to an embodiment of the present invention.
Figure 4:
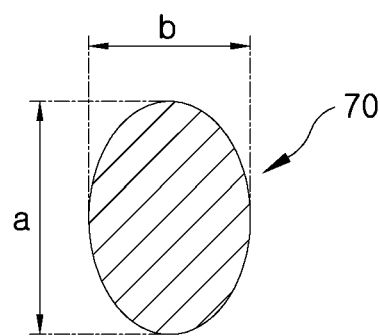
FIG. 4 is a cross-sectional view taken along line A-A' of FIG. 3.

With reference to FIGS. 1 to 4, a fixing system for cervical vertebrae according to an embodiment of the present invention will be described. FIG. 1 shows a state in which a fixing apparatus for cervical vertebrae according to an embodiment of the present invention is mounted in the cervical vertebrae, FIG. 2 is a schematic view showing an insertion driver that is used for a fixing apparatus for cervical vertebrae according to an embodiment of the present invention, FIG. 3 is a schematic view showing a loosening driver that is used for a fixing apparatus for cervical vertebrae according to an embodiment of the present invention, and FIG. 4 is a cross-sectional view taken along line A-A' of FIG. 3.

Referring to FIGS. 1 to 4, the fixing system for cervical vertebrae according to an embodiment of the present invention includes a fixing apparatus for cervical vertebrae, an insertion driver 50, and a loosening driver 60.

The fixing apparatus for cervical vertebrae is constituted of a cervical vertebrae-fixing plate 20 and a screw 40 that is inserted into cervical vertebrae 10, and serves to fix the cervical vertebrae 10. The screw 40 has a screw head with a screw groove including a center groove 41 and at least one slot 42 having a length equal to the diameter of the screw head, wherein the at least one slot 42 transverses the center groove 41 such that both ends of the at least one slot 42 open in a radial direction of the screw head. Specifically, as to the fixing apparatus for cervical vertebrae, a vertebral body in which a lesion is caused is removed, an artificial implant is inserted into a place in which the vertebral body is removed, and then the positional relationship between the inserted artificial implant and the neighboring vertebral body is fixed.

The cervical vertebrae-fixing plate 20 may be a plate-shaped metal plate, and a predetermined number of screw holes 25 are formed thereon. Through the screw holes 25 formed on the cervical vertebrae-fixing plate 20, the screw 40 may be inserted into the cervical vertebrae 10. In addition, clips 30 are provided in each of the screw holes 25, so that the screw 40 may be prevented from being easily shaken or escaped backward while holding the screw 40 inserted into the cervical vertebrae 10.

As to a structure in which the clips 30 are provided in the screw holes 25, two clips 30 may be provided in positions facing each other on the circumference of the screw holes 25, and in some cases, the number of the clips 30 to be provided and the position of the clips 30 to be provided on the circumference may vary.

Hereinafter, a process in which the cervical vertebrae-fixing plate 20 is fixed to the cervical vertebrae 10 will be described in more detail with reference to FIGS. 1 and 2. Six screw holes 25 are formed on the cervical vertebrae-fixing plate 20, and two clips 30 are provided in the positions facing each other on the circumference of each of the screw holes 25 and the provided clips may protrude from the inner circumference of each of the screw holes 25. A vertebral body in which a lesion is caused is removed, an artificial implant is inserted into a place in which the vertebral body is removed, the cervical vertebrae-fixing plate 20 is put to the inserted artificial implant and portions of the cervical vertebrae 10 in which the upper and lower vertebral bodies adjacent to the inserted artificial implant are positioned, and then the screw 40 is inserted into the cervical vertebrae 10 by turning the screw 40 having passed through the screw hole 25 using the insertion driver 50. The screw 40 inserted into the cervical vertebrae 10 in this manner is held by the clips 30 positioned in the screw hole 25 so that the separation of the screw 40 may be prevented.

The insertion driver 50 may enable the screw 40 to be inserted into the cervical vertebrae 10 by turning the screw 40, and the shape of a front end portion of the insertion driver 50 may vary depending on the shape of a groove on the screw 40 to be used, but the front end portion of the insertion driver 50 may have a hexagonal or star-like shape.

The loosening driver 60 is a driver that loosens the screw 40 inserted into the cervical vertebrae 10, and a convex portion 70 is formed at the rear of the front end portion of the loosening driver 60 which is fitted in the groove on the screw 40. The convex portion 70 may have a shape which ascends from a starting portion thereof towards a peak thereof and then descends from the peak towards a distal end portion thereof, and the cross-section of the convex portion 70 may have an oval shape.

Referring to FIGS. 3 and 4, as to the sizes of the convex portion 70, a distance between peaks out of the convex portion 70, which are vertically farthest from the main body of the loosening driver 60 and symmetrical to each other, that is, a major axis (a) of the cross-section having the largest area among the cross-sections of the oval-shaped convex portion 70 may be equal to a diameter of the screw hole 25 of the cervical vertebrae-fixing plate 20 or a diameter of the screw head of the screw 40. In addition, a minor axis (b) of the cross-section having the largest area among the cross-sections of the oval-shaped convex portion 70 may be equal to a distance between both clips 30 provided to face each other on the circumference of the screw hole 25.

In the process of an operation for the cervical vertebrae, there arises a case in which the screw 40 should be withdrawn because it is recognized that the size of the screw 40 to be inserted into the cervical vertebrae 10 is not tailored, but it is not easy to withdraw the inserted screw 40, and thereby it requires a lot of effort and time to remove the screw 40 in the process of the operation for the cervical vertebrae so that the operation time becomes longer and the smooth operation is not achieved.

In order to solve this problem, the convex portion 70 may be formed in the front end portion of the loosening driver 60, and spread the clips 30 while the screw 40 is loosened due to the sizes of the above-described cross-sections of the convex portion 70, and thereby the removal of the screw 40 may be facilitated. Specifically, the front end portion of the loosening driver 60 is fitted in the groove on the screw 40 held by the clips 30, and then the convex portion 70 of the loosening driver 60 spreads the clips 30 while the screw 40 is loosened by turning the loosening driver 60, and thereby the pressure applied to the screw 40 may be removed by the clips 30, so that the loosening or removal of the screw 40 inserted into the cervical vertebrae 10 may be facilitated.

As above, the fixing system for cervical vertebrae according to an embodiment of the present invention has been described, and hereinafter, a fixing system for cervical vertebrae according to another embodiment of the present invention will be described. The difference between the fixing system for cervical vertebrae according to an embodiment of the present invention and the fixing system for cervical vertebrae according to another embodiment of the present invention is that the convex portion is separately attached to the main body of the loosening driver as a replaceable portion as opposed to an integrated portion with respect to the main body of the loosening driver.

The convex portion according to another embodiment of the present invention may have various shapes and sizes, and in particular, the thickness of the peak portion of the convex portion may be varied, and an attachment groove may be provided in an attachment position of the loosening driver to which the convex portion is attached. The sizes of the screw holes and clips of the cervical vertebrae-fixing plate may be varied, and therefore the convex portion may be selected to conform to the sizes of the screw holes and clips, the selected convex portion may be mounted in the attachment groove of the loosening driver in such a manner as to be forcibly fitted therein, and then the operation for cervical vertebrae may be performed.

Thus, the loosening driver according to another embodiment of the present invention may be used for a variety of cervical vertebrae-fixing plates, and thereby the high compatibility may be realized and the convenience of the process of the operation for cervical vertebrae may be improved.

As described above, the loosening driver used for the fixing system for cervical vertebrae according to the embodiments of the present invention may include the convex portion formed in the front end portion thereof, and thereby the convex portion may spread the clips positioned in the screw holes of the cervical vertebrae-fixing plate, so that the removal of the screw may be facilitated in the process of the operation for cervical vertebrae, resulting in realizing the smooth operation for cervical vertebrae.

As described above, according to the embodiments of the present invention, there are provided the fixing system for cervical vertebrae in which an operation for cervical vertebrae may be smoothly performed by easily removing the screw inserted into the cervical vertebrae, and the driver used for The fixing apparatus for cervical vertebrae.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A system comprising:
   a cervical vertebrae-fixing plate having a screw hole;
   a screw configured to be inserted into the cervical vertebrae through the screw hole and having a screw head, wherein the screw head has a screw groove including a center groove and at least one slot having a length equal to the diameter of the screw head, wherein the at least one slot transverses the center groove and both ends of the at least one slot are open in a radial direction of the screw head;
   a first clip arm and a second clip arm disposed in positions facing each other on a circumference of the screw hole to elastically hold the screw;
   a driver having an elongated shape and configured to loosen the screw, the driver having a front end portion and a convex portion disposed at the rear of the front end portion,
   wherein the convex portion extends in a longitudinal direction of the driver and gradually ascends from the front end portion towards a peak of the convex portion and descends from the peak thereof, the convex portion having an oval shaped cross-section having a major axis and a minor axis, wherein the length of the major axis is equal to the diameter of the screw head,
   wherein when loosening the screw, the front end portion is inserted in the center groove and the convex portion is at least partially inserted in the at least one slot on the screw head which is held by the first and second clip arms, and the convex portion spreads the first and the second clip arms while the screw is loosened by turning the driver.

2. The system of claim 1, wherein the oval shaped cross-section of the convex portion is normal to an elongated direction of the driver.

3. The system of claim 1, wherein the cervical vertebrae-fixing plate is a metal plate.

4. A driver for loosening a screw from a cervical vertebrae-fixing plate having a screw hole,
   wherein the screw is configured to be inserted into the cervical vertebrae through the screw hole and has a screw head with a screw groove including a center groove and at least one slot having a length equal to the diameter of the screw head, wherein the at least one slot transverses the center groove such that both ends of the at least one slot are open in a radial direction of the screw head,
   wherein a first clip arm and a second clip arm are disposed in positions facing each other on a circumference of the screw hole to elastically hold the screw,
   wherein the driver having an elongated shape includes a front end portion and a convex portion disposed at the rear of the front end portion,
   wherein the convex portion extends in an elongated direction of the driver and gradually ascends from the front end portion towards a peak of the convex portion and descends from the peak thereof, the convex portion having an oval shaped cross-section having a major axis and a minor axis, wherein the length of the major axis is equal to the diameter of the screw head,
   wherein when loosening the screw, the front end portion is inserted in the center groove and the convex portion is at least partially inserted in the at least one slot on the screw head which is held by the first and second clip arms, and the convex portion spreads the first and the second clip arms while the screw is loosened by turning the driver.

5. The driver of claim 4, wherein the oval shaped cross-section of the convex portion is normal to an elongated direction of the driver.

* * * * *